(12) United States Patent
Guth et al.

(10) Patent No.: US 6,759,560 B2
(45) Date of Patent: Jul. 6, 2004

(54) METHOD FOR PRODUCING ALKALI METHYLATES

(75) Inventors: Josef Guth, Freinsheim (DE); Holger Friedrich, Bobenheim-Roxhiem (DE); Hans-Josef Sterzel, Dannstadt-Schauernheim (DE); Gerd Kaibel, Lampertheim (DE); Kirsten Burkart, Ludwigshafen (DE); Elke Hoffmann, Jena (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 54 days.

(21) Appl. No.: 10/148,929

(22) PCT Filed: Dec. 8, 2000

(86) PCT No.: PCT/EP00/12440
§ 371 (c)(1),
(2), (4) Date: Jun. 5, 2002

(87) PCT Pub. No.: WO01/42178
PCT Pub. Date: Jun. 14, 2001

(65) Prior Publication Data
US 2002/0183566 A1 Dec. 5, 2002

(30) Foreign Application Priority Data
Dec. 8, 1999 (DE) .......................................... 199 59 153

(51) Int. Cl.⁷ .............................................. C07C 31/30
(52) U.S. Cl. ....................................................... 568/851
(58) Field of Search .......................................... 568/851

(56) References Cited

U.S. PATENT DOCUMENTS

| | | | | |
|---|---|---|---|---|
| 2,877,274 A | * | 3/1959 | Kramis | 568/851 |
| 4,577,045 A | | 3/1986 | Matthes et al. | 568/851 |
| 4,895,989 A | | 1/1990 | Sander et al. | 568/851 |
| 5,053,560 A | | 10/1991 | Matthes et al. | 568/851 |
| 5,445,717 A | * | 8/1995 | Karki et al. | 205/471 |
| 5,897,748 A | * | 4/1999 | Kaibel | 203/1 |

FOREIGN PATENT DOCUMENTS

| | | | |
|---|---|---|---|
| DE | 968 903 | 4/1958 | |
| DE | 34 13 212 | 9/1985 | ............ C07C/31/30 |
| DE | 37 01 268 | 4/1988 | ............ C07C/31/30 |
| EP | 0 299 577 | 1/1989 | ............ C07C/29/70 |
| EP | 0 684 060 | 11/1995 | ............ B01D/3/20 |
| RO | 60485 | 6/1976 | ............ C07C/31/04 |
| SU | 165691 | 10/1964 | |

OTHER PUBLICATIONS

Jaeger Products, Inc. Fractionation Tray and Hardware Product bulletin 400.*
M. T. Tham, Distillation an introduction: Column Internals, 1997, pp. 1–4.*

* cited by examiner

Primary Examiner—Rosalynd Keys
(74) Attorney, Agent, or Firm—Keil & Weinkauf

(57) ABSTRACT

Alkali metal methoxides are prepared from aqueous alkali metal hydroxide, which may have been admixed with methanol, and methanol in a reaction column having at least 5, preferably from 15 to 30, theoretical plates between the feed point for the aqueous alkali metal hydroxide and the feed point for the methanol. The gaseous methanol/water mixture formed in the reaction is fractionated in a rectification column.

In one variant of the invention, the trays chosen for the reaction column configured as a bubble cap tray, valve tray or sieve tray column are trays in which not more than 5%, preferably <1%, of the liquid rains through the respective trays.

In another variant of the process of the present invention, the double-wall reaction column has a temperature in the double wall which is from 3 to 10° C. above the internal temperature in the column and is provided with random or ordered packing, where the average ratio of liquid flow to vapor flow is not exceeded by more than 15%, preferably not by more than 3%, in all subregions of the column cross section which correspond to more than 2% of the total column cross section.

16 Claims, 3 Drawing Sheets

METHOD FOR PRODUCING ALKALI METHYLATES

The present invention relates to a process for preparing alkali metal methoxides from aqueous alkali metal hydroxide, which may have been admixed with methanol, and methanol.

The preparation of alkoxides from alkali metal hydroxides and alcohols is known per se.

DE-C 968 903 has already described the continuous treatment of high-concentration aqueous alkali metal hydroxide solutions with a countercurrent of alcohol in a packed column, with the aqueous alkali metal hydroxide being able to be fed in at various places on the column in order to prevent blockage of the column by deposited alkali metal hydroxide. The alkoxide is formed by reaction of the alkali metal hydroxide located on the packing with the alcohol stream additionally passed through the column from the top downward.

However, low-boiling alcohols (methanol) can be used in this process only when a suitable auxiliary liquid is used for removing the water. This process also has the disadvantage that the deposits of solid alkali metal hydroxide which settle on the packing of the column can lead to blockage of the column. The procedure described in DE-C 968 903 does mention removal of the alcohol by azeotropic distillation using an entrainer, but in the procedure indicated the alcohol of the alcohol/water azeotrope which has been distilled off constantly has to be replaced, requiring a complicated recovery step.

SU-A 165 691 discloses a process for preparing sodium methoxide, which starts from a methanolic sodium hydroxide solution which is conveyed from a stirred vessel into the upper part of a continuously operated packed column in countercurrent to gaseous methanol.

The process requires a high energy input to achieve the appropriate product purity. It has the further disadvantage that solid sodium hydroxide is employed.

EP-A 0 299 577 describes a process for preparing alkoxides in which the water of reaction is removed by pervaporation. It is known that complete dewatering of the alcohol cannot be effected in this way.

DE-C 34 13 212 and DE-C 37 01 268 describe processes for preparing potassium tert-butoxide from aqueous potassium hydroxide and an excess of tert-butanol in a distillation column using an entrainer which, in contrast to the auxiliary liquid described in DE-C 968 903, does not form an azeotrope with water.

Furthermore, RO-A 60485 describes the isolation of sodium methoxide from anhydrous technical-grade methanol and technical-grade sodium hydroxide in a three-stage process with the aid of a hydrocarbon, in which process the water of reaction formed is removed by azeotropic distillation. The anhydrous hydrocarbon is recovered by fractional distillation with addition of $Na_2SO_4$. The sodium methoxide is obtained as a suspension in the hydrocarbon from which it can be filtered off.

These processes require additional separation operations and also leave extraneous materials in the alkali metal alkoxide solution. The latter interfere in further processing.

It has been found experimentally that the theoretical number of theoretical plates alone is not a sufficient criterion for an effective process for preparing substantially water-free alkoxide solutions. Thus, known processes for preparing alkoxides give only unsatisfactory qualities in which the water content is from about 0.5 to 2% based on the alkoxide, even in columns which have a high number of from 35 to 40 theoretical plates. These water contents are above those of commercial grades having a water content of about 0.1%.

It is an object of the present invention to provide a process for preparing alkoxide solutions which makes it possible to obtain a substantially water-free end product with justifiable energy input and in which no deposits are formed on the packing when a packed reaction column is used.

We have found that this object is achieved by the known process for preparing alkali metal methoxides from aqueous alkali metal hydroxide, which may have been admixed with methanol, and methanol in a reaction column having at least 5, preferably from 15 to 30, theoretical plates between the feed point for the aqueous alkali metal hydroxide and the feed point for the methanol, where in the case of a reaction column configured as a bubble cap tray, valve tray or sieve tray column, the trays are selected so that not more than 5%, preferably $\leq 1\%$, of the liquid rains through the respective trays.

For this embodiment of the process of the present invention, suitable columns are essentially bubble cap tray, valve tray and sieve tray columns. Specifically in the case of valve trays and sieve trays, the trays should be configured so that the raining-through of the liquid is minimized. A person skilled in the art will be familiar with the constructional measures required for this. Particularly tightly closing valve types are selected and thus, in particular, the vapor velocity into the tray openings is increased to double the value which is customarily set. This is achieved by a reduction in the number of valves. In the case of sieve trays, it is particularly useful to reduce the diameter of the openings in the tray and to maintain or even increase the number of openings.

In a variant of the present invention, the reaction column is provided with random packing elements or ordered packing, with ordered packing being preferred over random packing elements with a view to uniform distribution of the liquid. In this embodiment of the invention, the average ratio of liquid flow to vapor flow must not be exceeded by more than 15%, preferably not by more than 3%, in all subregions of the column cross section which correspond to more than 2% of the total column cross section. This low amount of liquid to be maintained according to the present invention obviously makes it possible for the capillary effect on the wire meshes to prevent local peak values of the liquid trickle density.

Suitable methods of achieving this are known from EP A 0 684 060. The desired characteristics of the liquid distribution can be achieved when using columns with random or ordered packing by the liquid trickle density in the marginal region of the column cross section next to the column wall, which region corresponds to about 2–5% of the total column cross section, being reduced by up to 100%, preferably by from 5 to 15%, compared to the remaining cross section. This can be achieved in a simple manner by targeted distribution of the drip points of the liquid distributors or their holes.

In this mode of operation, it is advantageous for the internal wall of the reaction column to be at a temperature which is from 3 to 10° C. above the temperature of the reaction column.

Owing to the very unfavorable position of the chemical equilibrium, breakthrough of even very small amounts of still water-containing liquid which have not come into contact with a sufficiently large amount of vapor obviously has to be prevented with certainty. Local breakthrough of water-containing liquid can obviously have a serious adverse effect on the quality of the product due to backreaction.

The combination of the process known per se for preparing alkali metal methoxides with the features of the invention which ensure that passage at the margins or stream formation or raining-through of liquid occurs at no point of the reaction column cross section results, in a surprising and synergistic fashion, in a purity of the alkali metal methoxide solution which has hitherto only been able to be achieved in the amalgam process or by the use of alkali metals.

It may be stated, and is advantageous for industrial implementation, that there are no additional constructional requirements in respect of the uniformity of the gas flow over the cross-sectional area of the column. It is not disadvantageous if the ratio of gas flow to liquid flow locally assumes higher values than the average value. Rather, increased gas flows locally improve water removal.

When carrying out the process of the present invention, no blockage occurs in a reaction column provided with random or ordered packing, and the methanol used can be recycled to the process without complicated work-up.

The process of the present invention can be carried out either batchwise or continuously.

In batchwise operation, the alcohol and the water are vaporized to the point at which the desired alkoxide concentration is present in the reaction mixture.

In the continuous process, an aqueous alkali metal hydroxide stream, which may have been admixed with methanol, is fed in at the top of the reaction column. The reaction column is operated as a pure stripping column. Methanol is fed in vapor form into the lower region of the column. In-specification alkoxide is obtained via the bottom offtake. The water-containing methanol stream leaving the top of the column is worked up in the rectification column. At the top of this column, the fresh methanol required is introduced. After partial condensation, a gaseous methanol stream having a very low water content is obtained at the top of the column and is recirculated to the lower region of the reaction column. The water is removed from the system via the bottoms from the rectification column.

The aqueous alkali metal hydroxide used in the process of the present invention is obtained by an electrochemical or a membrane process advantageously by a membrane process. In this way, it is possible to produce alkoxides which are completely free of mercury. In terms of the energy consumption, it is also advantageous for the aqueous alkali metal hydroxide to have a concentration of at least 30% preferably concentrated to the solubility limit and for it to be heated by means of a heat exchanger to close to the boiling point at the pressure prevailing in the reaction column prior to entering the reaction column.

The methanol is used in such an amount that it simultaneously serves as solvent for the alkali metal methoxide obtained. This amount should be selected so that the desired concentration of alkali metal methoxide, preferably 30%, is present in the bottoms from the reaction column.

The abovementioned condition for the amount of methanol to be used is met when the amount is from 10 to 50 times, preferably from 35 to 40 times, the mass of water which is introduced with the aqueous sodium hydroxide, or from 10 to 50 times, preferably from 30 to 40 times, the mass of water introduced with the aqueous potassium hydroxide.

In the process of the present invention, the reaction column is operated without reflux.

In the rectification column, a reflux ratio of at least 0.5, preferably from 0.8 to 1.4, is advisable when the vapor taken off at the top of the reaction column is fed, preferably in gaseous form, into the rectification column and the methanol obtained at the top of this, which has a water content of from 20 to 100 ppm, is recirculated, preferably in gaseous form, through a partial condenser and is subsequently fed via a vapor compressor to the lower end of the reaction column.

In one variant of the process of the present invention, the reflux ratio of the rectification column is at least 0.6, preferably from 0.8 to 1.4.

In this case, the vapor taken off at the top of the reaction column is passed through a vapor compressor upstream of the rectification column and the methanol then obtained in the rectification column, having a water content of from 20 to 100 ppm, is fed, preferably in gaseous form, via a partial condenser to the lower end of the reaction column.

The dimensions of the reaction column can be reduced in the lower region of the column if part of the methanol is introduced in gaseous form at the upper end or in the region of the upper end of the reaction column.

In this mode of operation according to the present invention, only part of the methanol stream, namely from 10 to 70%, preferably from 30 to 50%, is fed in at the lower end of the reaction column and the remaining part is introduced, either as a single stream or divided into a plurality of substreams, in gaseous form from 1 to 10, preferably from 1 to 3 theoretical plates below the feed point for the aqueous alkali metal hydroxide.

The dimensions of the reaction column can be reduced in the lower region of the column by the optional installation of one or more intermediate vaporizers in the upper region of the reaction column. In this configuration, it is also possible to introduce substreams of the methanol in liquid form into the upper region of the reaction column.

It is advantageous to operate the reaction column at a pressure of from 0.5 to 40 bar, preferably from 1 to 15 bar, particularly preferably from 3 to 10 bar, since smaller heat inputs and smaller amounts of methanol can be achieved at higher pressure.

The pressure in the rectification column can be chosen freely within a wide range. It is advisable to work at from about 1 to 4 bar. In the case of vapor compression, the pressure change between the two columns is advantageously chosen so that vapor compression for the methanol/water mixture or alternatively the methanol stream is readily possible.

The methanol necessary for the reaction and for dilution of the alkali metal methoxide solution is introduced at temperatures up to the boiling point, preferably at room temperature, at the top of the rectification column.

In a further embodiment of the invention, which is advantageous in respect of capital cost, the reaction column and rectification column are accommodated within a single outer column wall in which the lower region of the column is divided by a vertical dividing wall installed between the column walls so as to prevent cross-mixing of liquid and vapor streams in this subregion of the column, both parts of this longitudinally divided region have their own vaporizer via which the alkoxide solution or the water is taken off, the methanol obtained at the top of the column at a reflux ratio of at least 0.5, preferably from 0.8 to 1.4, which has a water content of from 20 to 100 ppm, is passed through a partial condenser and vapor compressor and then introduced at the lower end of the column in the subregion from which the alkoxide solution is taken off.

In this mode of operation, it is found to be useful to operate the column at a pressure of from 0.5 to 10 bar, preferably from 1 to 8 bar, particularly preferably from 3 to 5 bar.

BRIEF DESCRIPTION OF THE DRAWINGS

The process of the present invention can advantageously be carried out in a apparatus as shown schematically in FIGS. 1, 2 and 3.

Figure 1:
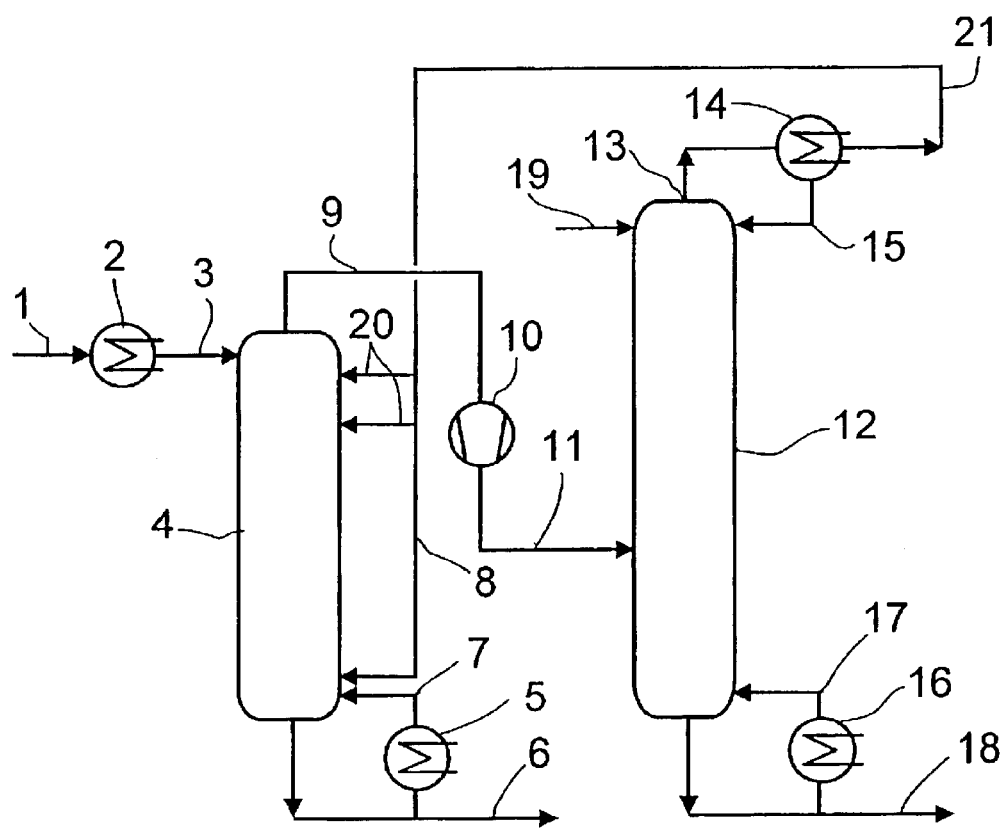
FIG. 1 shows an apparatus in which the aqueous alkali metal hydroxide is introduced via line 1 into a heat exchanger 2 in which it is heated to the temperature of the feed point, if desired partly vaporized and fed via line 3 to the top of the column 4. The alkali metal methoxide solution is taken off at the bottom of the column via line 6. At the bottom of the column there is a vaporizer 5 by means of which the concentration of the alkali metal methoxide solution is adjusted to the desired value. The vapor from the vaporizer is fed via line 7 to the lower end of the column. Gaseous methanol is likewise fed via line 8 to the lower end of the column. In addition to introduction via line 8, gaseous methanol can be introduced into the upper region of the column via one or more lines 20. At the top of the column, a methanol- and water-containing stream 9 is, without condensation, taken off in gaseous form, compressed via a vapor compressor 10 and fed via line 11 to the distillation column 12. At the bottom of this column, water is taken off via line 18. The column is heated by means of the vaporizer 16 which feeds the vapor stream via line 17 to the lower end of the column. At the top of the column, liquid methanol is introduced via line 19. The vapor stream obtained at the top of the column is passed via line 13 to the partial condenser 14 in which part of the vapor condenses and is fed in liquid form via line 15 to the top of the column and the remaining vapor stream is discharged via line 21 and introduced into the reaction column 4 via lines 8 and 20.
Figure 2:
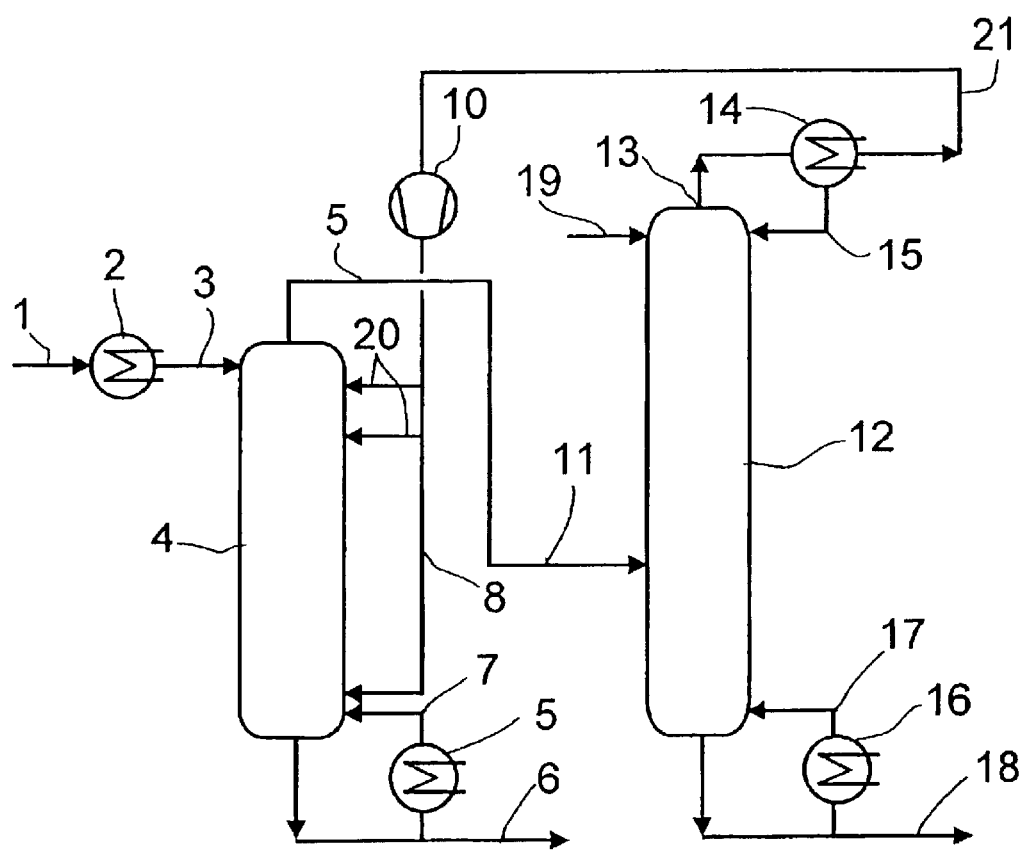
FIG. 2 shows a variant of the illustrative embodiment 1, in which the reaction column 4 is operated under a higher pressure than the column 12. The vapor stream 9 which is taken off at the top of the column 4 is fed directly into the column 12. The vapor stream 21 taken from the partial condenser 14 of the column 12 is conveyed via the compressor 10 and from there fed via lines 8 and 20 to the column 4.

At the lower end of the subregion 25 of the column, water is taken off via line 18.

The subregion 25 of the column is heated by means of the vaporizer 16 which feeds the vapor stream via line 17 to the lower end of the subregion 25 of the column. At the top of the column, liquid methanol is introduced via line 19. The vapor stream obtained at the top of the column is passed via line 13 to the partial condenser 14 in which part of the vapor is condensed and fed in liquid form via line 15 to the top of the column, and the remaining vapor stream is discharged via line 21, compressed in the vapor compressor 10 and fed via lines 8 and 20 to the subregion 24 of the column.

EXAMPLES

Example 1

27 g/h of a stream of 50% strength aqueous sodium hydroxide which has been heated to 75° C. is fed in at the top of a 1 m high column containing 3×3 mm wire mesh rings. This bed height corresponds to about 20 theoretical plates. The column is provided with a double wall which is divided transversely to the column into four chambers. A stream of oil heated to 80° C. is supplied to each chamber. The internal temperature of the column is 71–75° C. The column is operated without reflux. In this operating mode together with protective heating, the average ratio of liquid flow to vapor flow is exceeded by not more than 15% and passage at the margins is minimized by vaporization.

The column is operated at ambient pressure. At the lower end of the bed, 532 g/h of a liquid methanol stream containing about 20 ppm of water and having a temperature of 61° C. are fed in. The product stream from the bottom of the column (61 g/h) comprises 30% by weight of sodium methoxide in methanol and contains about 60 ppm of water and 410 ppm of sodium hydroxide. The temperature at the top of the column is 75° C. The stream taken off at the top comprises methanol having a water content of 3.93% by weight and has a mass flow of 498 g/h. This stream is fed in gaseous form into a second column at the level of the 5th theoretical plate. This second column has 40 bubble cap trays, corresponding to 29 theoretical plates, and is operated at atmospheric pressure. The reflux ratio is 1.3. The stream taken off at the top of the column after total condensation comprises about 30 ppm of water in methanol and has a flow of 478 g/h. In the condensate buffer, an amount of methanol corresponding to the methanol stream discharged from the plant (54 g/h) is fed in. The stream taken from the condensate vessel is fed to the reaction column. The bottoms (20 g/h) from the second column convey the water from the aqueous sodium hydroxide and the water formed in the reaction together with a residual methanol content of 1% by weight out of the system.

Comparative Example C2 (not according to the present invention)

29 g/h of a stream of 50% strength aqueous sodium hydroxide which has been heated to 75° C. is fed in at the top of a 1 m high column containing 3×3 mm wire mesh rings. This bed height corresponds to about 20 theoretical plates. The column is provided with a double wall which is divided transversely to the column into four chambers. The chambers are not supplied with heating medium. Passage of liquid at the margins along the column wall was observed. This liquid flow was about 3–5% of the total liquid flow. The column is operated at ambient pressure. At the lower end of the bed, 535 g/h of a liquid methanol stream containing about 20 ppm of water and having a temperature of 60° C. are fed in. The product stream from the bottom of the column (66 g/h) comprises 30% by weight of sodium methoxide in methanol and contains about 1070 ppm of water and 4060 ppm of sodium hydroxide. The column is operated without reflux and the temperature at the top of the column is 75° C. The stream taken off at the top comprises methanol having a water content of 4.2% by weight and has a mass flow of 498 g/h. This stream is fed in gaseous form into a second column at the level of the 5th theoretical plate. This second column has 40 bubble cap trays, corresponding to 29 theoretical plates, and is operated at atmospheric pressure. The reflux ratio is 1.3. The stream taken off at the top of the column after total condensation comprises about 30 ppm of water in methanol and has a flow of 477 g/h. In the condensate buffer, an amount of methanol corresponding to the methanol stream discharged from the plant (58 g/h) is fed in. The stream taken from the condensate vessel is fed to the reaction column. The bottoms (20 g/h) from the second column convey the water from the aqueous sodium hydroxide and the water formed in the reaction together with a residual methanol content of about 1% by weight out of the system.

Example 3

Figure 3:
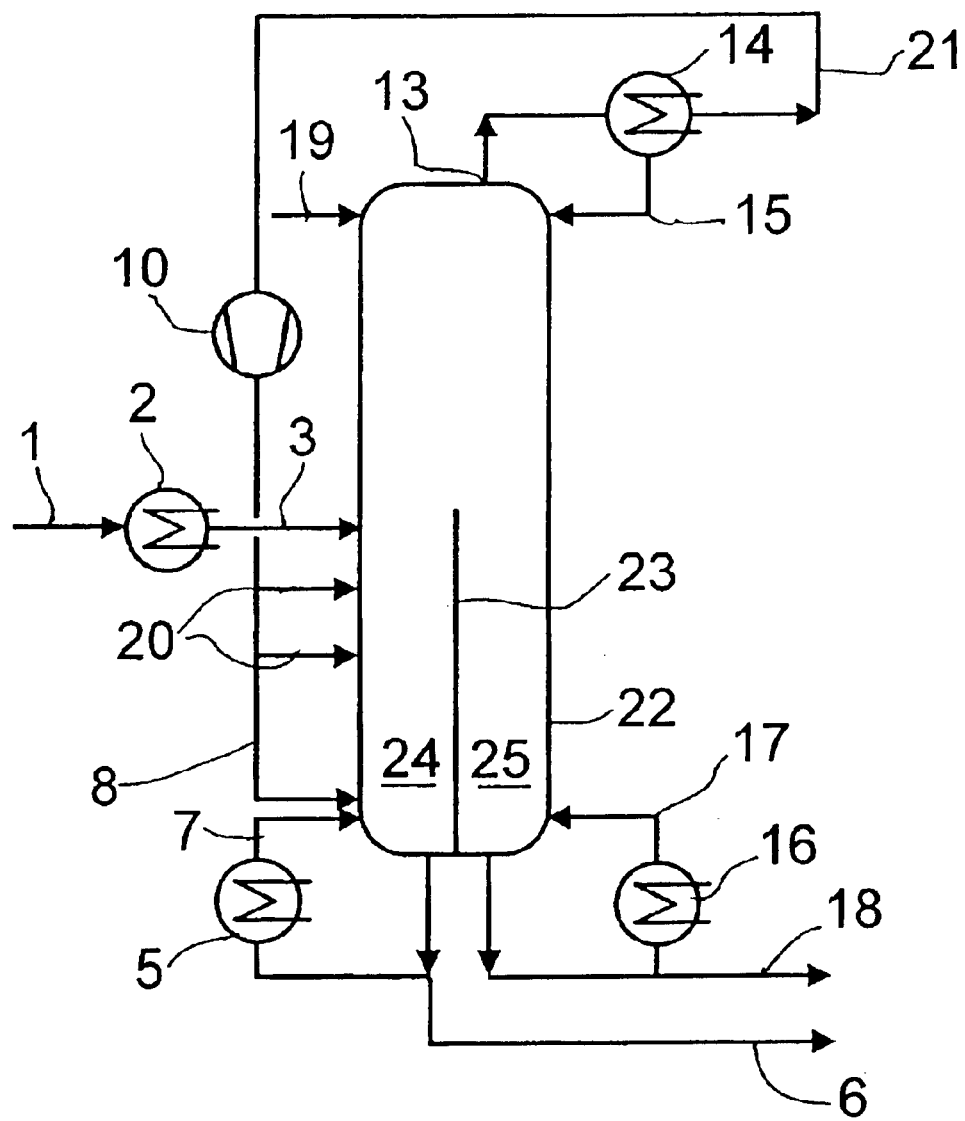
FIG. 3 shows an advantageous simplification of the apparatus in which the columns 4 and 12 shown in FIGS. 1 and 2 are combined into a single column 22. This column has in its lower region a dividing wall 23 which divides this region into two subregions 24 and 25. The aqueous alkali metal hydroxide is introduced via line 1 into a heat exchanger 2 in which it is heated to the temperature of the feed point, if desired partly vaporized and fed via line 3 into the subregion 24 of the column at the upper end of the dividing wall. At the lower end of the subregion 24 of the column, there is a vaporizer 5 by means of which the concentration of the alkali metal methoxide solution is adjusted to the desired value and the alkali metal methoxide solution is taken off via line 6. The vapor from the vaporizer is fed via line 7 to the lower end of the subregion 24 of the column. Likewise at the lower end of the subregion 24 of the column, gaseous methanol is fed in via line 8. In addition to introduction via line 8, gaseous methanol can be fed into the upper part of the subregion 24 of the column via one or more lines 20.

Example 3 describes the synthesis of sodium methoxide in a dividing wall column as shown in FIG. 3. At small column diameters as occur in the laboratory, it is simpler to construct the region of the dividing wall from two columns than to divide the corresponding column section. For this reason, the stripping section for the work-up by means of a dividing wall column was constructed as follows for the laboratory test: the section 24 consisted of a 1 m long bed of 3×3 mm wire mesh rings (20 theoretical plates), and the section 25 consisted of a column section containing 10 bubble cap trays (7 theoretical plates). The rectification section likewise consisted of a bed of 3×3 mm wire mesh rings having a length of 1 m (20 theoretical plates). The column section 24 was equipped with a double wall which was divided transversely to the column into four chambers. Each chamber was supplied with a stream of oil heated to 80° C. The internal temperature of the column was 71–75° C. Passage at the margins is thus avoided by means of vaporization.

The feed stream of 20 g/h comprised 50% strength aqueous sodium hydroxide at 75° C. This stream was fed into the column at the level of the 20th theoretical plate of the bed of wire mesh rings, i.e. at the upper end of section 24. The product stream (45 g/h) was discharged from the bottoms circuit of the section 24. It comprised sodium methoxide in a 69.5% strength methanol stream containing 460 ppm of sodium hydroxide and about 65 ppm of water. The temperature at the bottom was 71° C.

The trickle density in the region of the double wall was 0.007 l/cm$^2$ h over its entire length. This low trickle density ensures that the ratio of liquid flow to vapor flow is very constant over the column cross section due to the capillary effect in the bed and that deviations greater than 15% from the average value of this ratio do not occur.

The vapor stream leaving the uppermost part of the wire mesh ring bed went to the common rectification section. The column was operated at atmospheric pressure. The reflux ratio was 1.4. At the top of the column, a stream of methanol (50 g/h) containing about 25 ppm of water was obtained after total condensation and replacement of the methanol discharged from the system into the condensate receiver (40 g/h), and this methanol stream was fed back into the column section 24 at the level of the lower edge of the bed. At the lower end of the rectification section, there was a runback divider which was set so that all the downward-flowing stream was directed into the column section 25. The stream taken from the bottoms circuit of section 25 still contained about 1% by weight of methanol and amounted to 15 g/h.

We claim:

1. A process for preparing alkali metal methoxides from aqueous alkali metal hydroxide, which may have been admixed with methanol, and methanol in a reaction column (4) having at least 5 theoretical plates between the feed point for the aqueous alkali metal hydroxide (3) and the feed point for the methanol (8) with fractionation of the gaseous methanol/water mixture formed in the reaction in a rectification column (12), wherein
    a) the trays selected for the reaction column (4) configured as a bubble cap tray, valve tray or sieve tray column are trays in which not more than 5% of the liquid rains through the respective trays, or
    b) the reaction column (4) is provided with random packaging or ordered packaging and the average ratio of liquid flow to vapor flow is not exceeded by more than 15% with regard to the liquid in all subregions of the column cross section which correspond to more than 2% of the total column cross section, by reducing the liquid trickle density in the marginal region of the column cross section next to the column wall, which region corresponds to about 2–5% of the total column cross section, by up to 100% compared to the remaining cross section, and by keeping the internal column wall of the reaction column (4), (24) provided with random packaging or ordered packing is at a temperature which is from 3 to 10° C. above the internal temperature of the reaction column, and wherein the reaction column is operated without reflux, and wherein the reaction column and the rectification column are either individual columns (4) and (12) or are accommodated within a single outer column wall (22).

2. A process as claimed in claim 1, wherein the aqueous alkali metal hydroxide is prepared electrochemically.

3. A process as claimed in claim 1, wherein the aqueous alkali metal hydroxide is prepared by means of a membrane process.

4. A process as claimed in claim 1, wherein the aqueous alkali metal hydroxide solution has a concentration of at least 30% and is heated by means of a heat exchanger (2) to close to the boiling point at the pressure prevailing in the reaction column prior to entering the reaction column (4), (24).

5. A process as claimed in claim 1, wherein the aqueous alkali metal hydroxide solution is concentrated to the solubility limit, and is heated by means of a heat exchanger (2) to close to the boiling point at the pressure prevailing in the reaction column prior to entering the reaction column (4), (24).

6. A process as claimed in claim 1, wherein the mass of methanol is from 10 to 50 times the mass of water which is introduced with the aqueous alkali metal hydroxide when the alkali metal hydroxide is sodium hydroxide or potassium hydroxide.

7. A process as claimed in claim 1, wherein the methanol having a water content of from 20 to 100 ppm formed from the methanol/water mixture in the rectification column (12), (25) at a reflux ratio of at least 0.5 is recirculated via a partial condenser (14) and vapor compressor (10) to the lower end of the reaction column (4), (24).

8. A process as claimed in claim 7, wherein only part, namely from 10 to 70% of the methanol stream obtained after the rectification, which has a water content of from 20 to 100 ppm, is fed in at the lower end of the reaction column (4), (24) and the remaining part is introduced, as a single stream or divided into a plurality of substreams (20), in gaseous form below the feed point for the aqueous alkali metal hydroxide (3).

9. A process as claimed in claim 1, wherein fresh methanol at temperatures up to the boiling point is fed in at the top (19) of the rectification column (12).

10. A process as claim in claim 1, wherein the reaction column (4) and the rectification column (12) are individual columns.

11. A process as claimed in claim 10, wherein the methanol having a water content of from 20 to 100 ppm formed from the methanol/water mixture in the rectification column (12) with upstream vapor compressor (10) at a reflux ratio of at least 0.6 is recirculated via a partial condenser (14) to the reaction column (4).

12. A process as claimed in claim 10, wherein the reaction column (4) is operated at a pressure of from 0.5 to 40 bar.

13. A process as claimed in claim 1, wherein the reaction column and the rectification column are accommodated within a single outer column wall (22) in which the lower region of the column is divided by a vertical dividing wall (23) installed between the column walls so as to prevent cross-mixing of liquid and vapor streams in this subregion of the column, both parts of this longitudinally divided region have their own vaporizer (5), (16) via which the alkoxide solution (6) or the water (18) is taken off.

14. A process as claimed in claim 13, wherein the aqueous alkali metal hydroxide having a concentration of at least 30% and heated to close to the boiling point is introduced (3) at the upper end of the dividing wall (23) into the subregion where the alkoxide solution is taken off (24).

15. A process as claimed in claim 13, wherein the column (22) is operated at a pressure of from 0.5 to 10 bar.

16. The process of claim 8, wherein the feed point is 1 to 10 theoretical plates below the feed point for the aqueous alkali metal hydroxide (3).

* * * * *